United States Patent
Yamamoto et al.

(10) Patent No.: US 6,914,152 B2
(45) Date of Patent: Jul. 5, 2005

(54) METHOD FOR PRODUCING BIPHENYL AND ITS DERIVATIVES

(75) Inventors: Yasushi Yamamoto, Yamaguchi (JP); Tetsuro Tsuji, Yamaguchi (JP); Jun Haruta, Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 10/261,443

(22) Filed: Oct. 2, 2002

(65) Prior Publication Data

US 2003/0088120 A1 May 8, 2003

(30) Foreign Application Priority Data

Oct. 9, 2001 (JP) ........................................ 2001-310899

(51) Int. Cl.$^7$ .......................... C07C 69/76; C07C 13/28; C07F 15/00
(52) U.S. Cl. ............................. 560/76; 544/225; 546/2; 585/422
(58) Field of Search .................... 560/76, 96; 544/225; 546/2; 585/422

(56) References Cited

U.S. PATENT DOCUMENTS 4,581,469 A * 4/1986 Itatani et al. ................. 560/96

FOREIGN PATENT DOCUMENTS

| JP | 55-141417 | | 11/1980 |
| JP | 60051150 A | * | 3/1985 |
| JP | 60051151 A | * | 3/1985 |
| JP | 61-106541 | | 5/1986 |

OTHER PUBLICATIONS

Jerry March, Advanced Organic Chem. $2^{nd}$. ed. McGraw–Hill Book Co. p. 463–469, 1979.*

* cited by examiner

Primary Examiner—Cecilia J. Tsang
Assistant Examiner—Taylor V. Oh
(74) Attorney, Agent, or Firm—Young & Thompson

(57) ABSTRACT

A method for producing biphenyl and its derivative comprising oxidatively coupling a benzene aromatic compound in the presence of a catalyst comprising a palladium salt, a copper salt, and a bidentate ligand compound capable of forming a complex with the palladium salt via the nitrogen atom and the oxygen atom in the molecule thereof in an atmosphere containing molecular oxygen. In particular, an improved method for selectively producing an asymmetrically substituted biphenyl derivative, such as a 2,3,3',4'-biphenyltetracarboxylic acid tetraester, which comprises oxidatively coupling a substituted aromatic compound, such as a phthalic diester, in the presence of the catalyst in an atmosphere containing molecular oxygen without replenishing with a ligand.

6 Claims, No Drawings

METHOD FOR PRODUCING BIPHENYL AND ITS DERIVATIVES

BACKGROUND OF THE INVENTION

1. Field of the Invention

The present invention relates to a method for producing biphenyl and its derivative by oxidative coupling of a benzene aromatic compound in a reaction system containing a palladium salt, a copper salt, and a bidentate ligand compound capable of forming a complex with the palladium salt via the nitrogen atom and the oxygen atom present in its molecule and in an atmosphere containing molecular oxygen preferably at a high temperature. More particularly, it relates to a method for selectively producing an asymmetrically substituted biphenyl derivative such as a 2,3,3',4'-biphenyltetracarboxylic acid tetraester (hereinafter abbreviated as a-BPTT) by using a substituted aromatic compound such as a phthalic diester as the benzene aromatic compound.

2. Description of Related Art

JP-A-55-141417 proposes a process of preparing a biphenyl which comprises oxidatively coupling a benzene aromatic compound in a molecular oxygen atmosphere in the presence of an organopalladium salt and an organocopper salt. Applying the process to oxidative coupling of a phthalic diester yields a 3,3',4,4'-biphenyltetracarboxylic acid tetraester (hereinafter abbreviated as s-BPTT) and an a-BPTT with the production ratio of the former being higher than that of the latter.

JP-A-61-106541 proposes a method for improving production selectivity to an asymmetrically substituted biphenyl derivative such as an a-BPTT in oxidative coupling of a substituted aromatic compound such as a phthalic diester. However, this method requires continuous or intermittent replenishment of the reaction system with a β-diketone as a ligand with the progress of the reaction.

SUMMARY OF THE INVENTION

It is an object of the present invention to provide a novel method for producing biphenyl and its derivative by oxidative coupling of a benzene aromatic compound. In particular, the object is to provide an improved method for selectively producing an asymmetrically substituted biphenyl derivative such as a 2,3,3',4'-biphenyltetracarboxylic acid tetraester by oxidative coupling of a substituted aromatic compound such as a phthalic diester without replenishing with a ligand.

The above object of the invention is accomplished by a method for producing biphenyl and its derivative comprising oxidatively coupling an aromatic compound represented by formula (1):

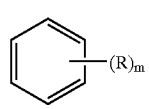

(1)

wherein R represents a substituent, and m represents an integer of 0 to 4, in the presence of a palladium salt, a copper salt, and a bidentate ligand compound capable of forming a complex with the palladium salt via the nitrogen atom and the oxygen atom in the molecule thereof in an atmosphere containing molecular oxygen.

DESCRIPTION OF THE EMBODIMENT

Preferred embodiments of the present invention are enumerated below.

1) The method for producing a biphenyl derivative, wherein the aromatic compound represented by formula (1) is one in which m is an integer of 1 to 3, which is oxidatively coupled in the presence of a palladium salt, a copper salt, and a bidentate ligand compound capable of forming a complex with the palladium salt via the nitrogen atom and the oxygen atom in the molecule thereof in an atmosphere containing molecular oxygen without replenishing with a ligand to selectively produce an asymmetrically substituted biphenyl derivative.

2) The method for producing a biphenyl derivative as set forth in 1), wherein the aromatic compound represented by formula (1) is a phthalic diester, and an a-BPTT (2,3,3',4'-biphenyltetracarboxylic acid tetraester) is selectively produced.

3) The method for producing a biphenyl derivative as set forth in 1) or 2), wherein the production molar ratio of an asymmetrically substituted biphenyl derivative to the produced biphenyl derivatives, i.e., an asymmetrically substituted biphenyl derivative/(symmetrically substituted biphenyl derivative+asymmetrically substituted biphenyl derivative) ratio is 0.6 to 0.99.

4) The method for producing a biphenyl derivative as set forth in any one of 1), 2), and 3), wherein the oxidative coupling is carried out at a temperature of 50 to 300° C.

5) The method for producing a biphenyl derivative as set forth in any one of 1) to 4), wherein the bidentate ligand compound is a nitrogen-containing heterocyclic compound having an oxygen-containing substituent and represented by formula (2):

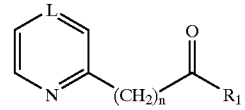

(2)

wherein $R_1$ represents an alkyl group, an aryl group, an alkoxy group, an amino group or a hydroxyl group; L represents CH or N; and n represents an integer of 0 to 3.

6) The method for producing a biphenyl derivative as set forth in any one of 1) to 4), wherein the bidentate ligand compound is a nitrogen-containing heterocyclic compound having an oxygen-containing substituent and represented by formula (3):

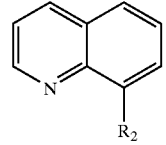

(3)

wherein $R_2$ represents a hydroxyl group or $COR_1$; and $R_1$ represents an alkyl group, an aryl group, an alkoxy group, an amino group or a hydroxyl group.

7) The method for producing a biphenyl derivative as set forth in any one of 1) to 4), wherein the bidentate ligand compound is an amino compound represented by formula (4):

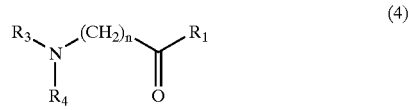

wherein $R_1$ represents an alkyl group, an aryl group, an alkoxy group, an amino group or a hydroxyl group; $R_3$ and $R_4$ each represent a hydrogen atom, an alkyl group or an aryl group; and n represents an integer of 0 to 3.

8) The method for producing a biphenyl derivative as set forth in any one of 1) to 7), wherein the oxidative coupling is a substantially solventless reaction.

The aromatic compound used in the present invention is a benzene aromatic compound represented by formula (1). In formula (1) the substituent R includes an alkyl group having 1 to 5 carbon atoms, an alkoxy group having 1 to 5 carbon atoms, an alkoxycarbonyl group having 1 to 5 carbon atoms, an aryloxycarbonyl group, an alkanoyloxy group having 1 to 5 carbon atoms, an alkanoyloxyalkyl group having 1 to 5 carbon atoms, an alkyl group having 1 to 5 carbon atoms, the hydrogen atom of which is substituted with an acetyl group or a halogen atom, a nitro group, and a halogen atom.

Specific examples of the benzene aromatic compound represented by formula (1) are benzene, toluene, ethylbenzene, 1,2,4-trimethylbenzene, o-xylene, m-xylene, p-xylene, anisole, methyl benzoate, butyl benzoate, methyl toluylate, acetylbenzene, 2,6-dimethylbenzyl acetate, xylylene diacetate, nitrobenzene, o-chloromethylbenzene, chlorobenzene, benzene fluoride, o-chlorotoluene, trifluorotoluene, phthalic diesters, isophthalic diesters, and terephthalic diesters.

The phthalic diesters, isophthalic diesters and terephthalic diesters supra are diester compounds obtained by reacting the corresponding acid, an anhydride thereof or an acid halide thereof with a compound having a hydroxyl group at the terminal, such as a lower aliphatic alcohol or an aromatic alcohol.

The palladium salt which can be used in the present invention includes salts between inorganic acids and palladium, such as palladium chloride, palladium bromide, palladium iodide, palladium hydroxide, palladium nitrate, and palladium sulfate; and salts between organic acids or diketone compounds and palladium, such as palladium acetate, palladium propionate, palladium pivalate, palladium trifluoroacetate, palladium trifluoromethanesulfonate, bisacetylacetonatopalladium, and bis(hexafluoroacetylacetonato)palladium. Palladium acetate, palladium trifluoroacetate, palladium nitrate, bis(acetylacetonato) palladium, and palladium hydroxide are particularly preferred. The palladium salt is preferably used in an amount of $1 \times 10^{-5}$ mol or more, particularly $5 \times 10^{-5}$ or more, and 0.05 mol or less, particularly 0.01 mol or less, per mole of the starting benzene aromatic compound. In amounts less than $1 \times 10^{-5}$ mol, the reaction is inefficient. Amounts more than 0.05 mol, which mean increased amounts of expensive palladium, are uneconomical.

The bidentate ligand compound which can be used in the present invention is a compound having bidentate coordinating capability through the oxygen atom and the nitrogen atom in the molecule thereof to form a complex with the palladium salt. It includes a nitrogen-containing heterocyclic compound having an oxygen-containing substituent, such as the compound represented by formulae (2) or (3) and an amine having an oxygen-containing substituent, such as the amino compound represented by formula (4). Specific examples of the bidentate ligand compounds are pyridinecarboxylic acid, methyl pyridinecarboxylate, ethyl pyridinecarboxylate, pyrazinecarboxylic acid, methyl pyrazinecarboxylate, ethyl pyrazinecarboxylate, quinolinecarboxylic acid, isoquinolinecarboxylic acid, hydroxyquinoline, 2-benzoylpyridine, 2-pyridylamide, N,N-dimethylglycine, and N,N-dimethylacetamide. In particular, 2-pyridinecarboxylic acid and 2-pyrazinecarboxylic acid are preferred.

The bidentate ligand compound may be added to the reaction system either as such or in the form of a palladium complex having the bidentate ligand bonded to palladium via the nitrogen atom and the oxygen atom which is previously prepared by treating the bidentate ligand compound with the palladium salt.

The bidentate ligand compound is preferably used in an amount of 0.5 to 4 mol, particularly 1 to 2 mol, per mole of the palladium salt.

It is not necessary to continuously or intermittently add the bidentate ligand compound to the reaction system.

The copper salt which can be used in the present invention includes copper salts of aliphatic carboxylic acids having 1 to 10 carbon atoms, such as formic acid, acetic acid, trifluoroacetic acid, n-butyric acid, 2-methylpropionic acid, pivalic acid, lactic acid, butyric acid, propionic acid, and valeric acid; copper salts of aromatic carboxylic acids, such as benzoic acid and phthalic acid; and copper salts of β-diketones, such as acetylacetone, benzoylacetone, and trifluoroacetylacetone. Additionally included are copper halides, such as copper chloride, copper bromide, and copper iodide, and inorganic copper salts, such as copper nitrate, copper sulfate, and copper hydroxide.

The copper salt is used in an amount of 0.01 to 10 mol, preferably 0.05 to 3 mol, per mole of the bidentate ligand compound. A copper salt less than 0.01 mol results in failure to secure a sufficient reaction rate. A copper salt more than 10 mol suppresses the reaction.

The reaction temperature of the oxidative coupling in the present invention is preferably 50° C. or higher, still preferably 100° C. or higher, and 300° C. or lower, still preferably 250° C. or lower. Coupling reaction hardly occurs at temperatures lower than 50° C. Reaction temperatures exceeding 300° C. result in reduced production of the desired biphenyl or biphenyl derivative.

In the present invention molecular oxygen may be fed in the form of pure oxygen gas, which involves a danger of explosion. It is advisable for safety to use an inert gas (e.g., nitrogen or carbonic acid gas) diluted oxygen-containing gas or air.

The reaction pressure in the present invention, in terms of oxygen partial pressure (the initial pressure in case of a closed reaction system), is suitably 0.01 atm or higher, preferably 0.05 atm or higher, still preferably 0.1 atm or higher, and 200 atm or lower, preferably 50 atm or lower, still preferably 30 atom or lower. In conventional known oxidative coupling reaction systems, the palladium catalyst component precipitates as palladium black to lose its catalytic activity under an oxygen partial pressure lower than 0.05 atm. In the present invention precipitation of palladium black does not happen even under an oxygen partial pressure lower than 0.05 atm so that effective catalytic action can be maintained.

Oxygen gas or oxygen-containing gas can be fed to the reaction system either in a closed system or a flow system. Where fed in a flow system, an inert gas-diluted oxygen-containing gas (preferably having an oxygen content of about 10 to 40 vol%) or air is preferably bubbled through the reaction mixture at a flow rate of about 1 to 2000 ml/min, particularly 10 to 1000 ml/min, per 100 ml of the total of gas and the reaction liquid.

The reaction can be carried out with or without a solvent. It is advisable for industrial production to conduct the reaction with substantially no solvent. In cases where a reaction solvent is used, usable solvents include organic acid esters, such as ethylene glycol diacetate and dimethyl adipate, and ketones, such as n-butyl methyl ketone, methyl ethyl ketone, and isopropyl ethyl ketone. The amount of the solvent, if used, is, for example, not more than 10000 times, preferably not more than 1000 times, the volume of the starting benzene aromatic compound.

The product obtained by the method of the invention includes biphenyl and its derivatives inclusively represented by formula (5):

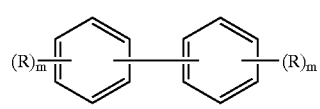

(5)

wherein R represents a substituent; and m represents an integer of 0 to 4.

Starting with benzene, for example, results in production of biphenyl. Starting with toluene or xylene yields bitolyl or tetramethylbiphenyl, respectively. Starting with a phthalic diester furnishes a biphenyltetracarboxylic acid tetraester.

Oxidative coupling of the substituted aromatic compound according to the method of the invention yields isomers: a symmetrically substituted biphenyl derivative (a biphenyl derivative having substituents on the two benzene rings in a symmetric configuration, hereinafter referred to as an s-compound) and an asymmetrically substituted biphenyl derivative (a biphenyl derivative having substituents on the two benzene rings in an asymmetric configuration, hereinafter referred to as an a-compound). The method of the present invention is characterized by its capability to selectively produce the asymmetrically substituted biphenyl derivative (a-compound).

For instance, where starting with a phthalic diester, there are produced a 2,3,3',4'-biphenyltetracarboxylic acid tetraester (a-BPTT) and a 3,3',4,4'-biphenyltetracarboxylic acid tetraester (s-BPTT), with little production of a 2,2',3, 3'-biphenyltetracarboxylic acid tetraester. According to the method of the invention, the 2,3,3',4'-biphenyltetracarboxylic acid tetraester can selectively be obtained as a main product.

Where starting with o-xylene, there are produced 2,3,3', 4'-tetramethylbiphenyl and 3,3',4,4'-tetramethylbiphenyl, with little production of 2,2',3,3'-tetramethylbiphenyl. According to the method of the invention, 2,3,3',4'-tetramethylbiphenyl can selectively be obtained as a main product.

The selectivity to such an asymmetrically substituted biphenyl derivative can be increased to 60 to 99%, particularly 70 to 95%, by properly choosing the reaction conditions.

The term "selectivity" as referred to above denotes a percentage of an asymmetrically substituted biphenyl derivative to the produced biphenyl derivatives, i.e., an asymmetrically substituted biphenyl derivative/ (symmetrically substituted biphenyl derivative+ asymmetrically substituted biphenyl derivative) molar ratio.

The produced biphenyl or biphenyl derivative is isolated and purified by well-known procedures, such as distillation and crystallization.

The resulting biphenyl derivative, for example, a-BPTT is hydrolyzed in a known manner, such as hydrolysis under high temperature and high pressure conditions or hydrolysis with an acid or an alkali, to give 2,3,3',4'-biphenyltetracarboxylic acid. The acid can be converted to 2,3,3',4'-biphenyltetracarboxylic acid dianhydride by heating at a high temperature. The resulting dianhydride is useful as one of monomers for the manufacture of aromatic polyimide.

The present invention will now be illustrated in greater detail with reference to Examples, but it should be understood that the present invention is not construed as being limited thereto.

In Examples conversions and coupling yields are those of benzene aromatic compounds charged.

A conversion and a coupling yield of a benzene aromatic compound charged and an s-compound/a-compound production ratio were calculated in accordance with the following equations on a molar basis.

1) Conversion (%)=(amount of aromatic compound consumed)/(amount of aromatic compound charged)×100
2) Coupling yield (%)=2×(amount of coupling product)/ (amount of aromatic compound charged)×100
3) s-Compound/a-compound production ratio=(s-compound yield)/(a-compound yield), (s-compound yield)+(a-compound yield) being taken as 100.

EXAMPLE 1

Into a 20 ml pear flask was weighed 1.27 g (6.5 mmol) of dimethyl phthalate, and 0.05 mmol of palladium trifluoroacetate (Pd(OCOCF$_3$)$_2$), 0.015 mmol of copper acetate monohydrate (Cu(OAc)$_2$.H$_2$O), and 0.05 mmol of 2-pyridinecarboxylic acid (represented by formula (6); hereinafter abbreviated as pyca) were put therein as catalyst components. A Liebig condenser was fitted to the flask. The inner atmosphere was displaced with grade A air with a dew point of −80° C. or lower under atmospheric pressure and sealed the flask off with a balloon containing air as a cap. Cooling water at 5° C. was circulated through the Liebig condenser. The flask was maintained in a silicone oil bath previously heated to 200° C. for a reaction time of 6 hours while stirring with a magnetic stirrer at 600 rpm. After the reaction, the flask was cooled with water, and the contained gas was purged. The contents were washed with acetone and analyzed by gas chromatography to determine the conversion of dimethyl phthalate and the coupling product. The results are shown in Table 1.

COMPARATIVE EXAMPLE 1

The procedures of Example 1 were followed, except for replacing pyca with the same molar quantity of 1,10-phenanthroline (formula (7), hereinafter abbreviated as 1,10-phen). The analytical results are shown in Table 1.

EXAMPLE 2

The procedures of Example 1 were followed, except for replacing $Pd(OCOCF_3)_2$ with the same molar quantity of palladium acetate $(Pd(OAc)_2)$. The analytical results are shown in Table 1.

COMPARATIVE EXAMPLE 2

The procedures of Example 2 were followed, except for replacing pyca with the same molar quantity of 1,10-phen. The analytical results are shown in Table 1.

EXAMPLE 10

Into a 50 ml three-necked flask were weighed 25.0 g (129 mmol) of dimethyl phthalate, 0.135 mmol of $Pd(OCOCF_3)_2$, 0.135 mmol of pyca, and 0.041 mmol of $Cu(OAc)_2.H_2O$. A Liebig condenser, a gas feed tube, and a thermometer were fitted to the flask. Cooling water at 5° C. was circulated through the Liebig condenser. Grade A air with a dew point of −80° C. or lower under atmospheric pressure was fed through the gas feed tube at a rate of 50 ml/min. The flask was maintained in a silicone oil bath previously heated to 80° C. to dissolve the catalyst. After the catalyst dissolved, the bath temperature was set to keep the reaction mixture at 200° C. to allow the reaction mixture to react for 1 hour. Thereafter, the reaction product was analyzed in the same manner as in Example 1. The results obtained were as shown in Table 1.

TABLE 1

| | Complex | | | | | s-BPTT/ |
| | Pd Salt | Bidentate Ligand Compound | Reaction Temp. (° C.) | Conversion (%) | Coupling Yield (%) | a-BPTT production ratio |
| --- | --- | --- | --- | --- | --- | --- |
| Example 1 | $Pd(OCOCF_3)_2$ | pyca | 200 | 20.1 | 12.0 | 11/89 |
| Comparative Example 1 | $Pd(OCOCF_3)_2$ | 1,10-phen | 200 | 17.3 | 8.8 | 88/12 |
| Example 2 | $Pd(OAc)_2$ | pyca | 200 | 7.6 | 4.6 | 16/84 |
| Comparative Example 2 | $Pd(OAc)_2$ | 1,10-phen | 200 | 22.3 | 12.1 | 91/9 |
| Example 3 | Pd(pyca) (acac) | | 200 | 20.0 | 11.9 | 10/90 |
| Example 4 | $Pd(OCOCF_3)_2$ | (8) | 200 | 16.0 | 10.2 | 10/90 |
| Example 5 | $Pd(OCOCF_3)_2$ | (9) | 200 | 12.2 | 6.1 | 14/86 |
| Example 6 | $Pd(OCOCF_3)_2$ | (10) | 200 | 11.0 | 6.0 | 17/83 |
| Example 7 | $Pd(OCOCF_3)_2$ | (11) | 200 | 7.8 | 4.6 | 14/86 |
| Example 8 | $Pd(OCOCF_3)_2$ | (12) | 200 | 8.3 | 4.5 | 13/87 |
| Example 9 | $Pd(OCOCF_3)_2$ | (13) | 200 | 11.5 | 6.4 | 17/83 |
| Example 10 | $Pd(OCOCF_3)_2$ | pyca | 200 | 7.0 | 3.5 | 8/92 |

EXAMPLE 3

In 10 ml of acetone was dissolved 0.20 mmol of bis(acetylacetonato)palladium $(Pd(acac)_2$, wherein acac stands for acetylacetonato group), and 0.20 mmol of pyca was added to the solution at room temperature. The solvent was removed from the solution by evaporator to give a crude complex, which was washed three times with 10 ml portions of hexane to remove any residual acetylacetone and dried at room temperature under reduced pressure to obtain a complex, Pd(pyca)(acac). The procedures of Example 1 were followed, except for using 0.05 mmol of the resulting complex in place of $Pd(OCOCF_3)_2$ and pyca. The analytical results are shown in Table 1.

EXAMPLES 4 TO 9

The procedures of Example 1 were followed, except for replacing pyca with the same molar amount of each of bidentate ligand compounds represented by formulae (8) to (13). The analytical results obtained are shown in Table 1.

EXAMPLE 11

A glass tube inserted into a 50 ml pressure-resistant SUS-made autoclave was charged with 9.70 g (91.5 mmol) of o-xylene, 0.09 mmol of $Pd(OCOCF_3)_2$, 0.03 mmol of $Cu(OAc)_2.H_2O$, and 0.10 mmol of pyca. The autoclave was closed, and an oxygen/nitrogen mixed gas ($O_2/N_2$=50/50 by vol %) was introduced into the autoclave under a gauge pressure of 50 kg/cm². The autoclave was immersed in an oil bath previously heated to 150° C. to allow the mixture to react. After 5 hours, the autoclave was taken out of the bath, cooled to room temperature, and the inner gas was released. The resulting reaction mixture was analyzed by gas chromatography. The results obtained are shown in Table 2.

COMPARATIVE EXAMPLE 3

The procedures of Example 11 were followed, except for replacing $Pd(OCOCF_3)_2$ and pyca with the same molar amounts of Pd(OAc)₂ and 1,10-phen, respectively. The analytical results were as shown in Table 2.

TABLE 2

| | Pd Salt | Bidentate Ligand Compound | Reaction Temp. (° C.) | Conversion (%) | Coupling Yield (%) | s-tetramethylbiphenyl/ a-tetramethylbiphenyl production ratio* |
|---|---|---|---|---|---|---|
| Example 11 | Pd(OCOCF₃)₂ | pyca | 150 | 30.1 | 8.3 | 30/70 |
| Comparative Example 3 | Pd(OAc)₂ | 1,10-phen | 150 | 23.6 | 4.7 | 74/26 |

*: s-tetramethylbiphenyl: 3,3',4,4'-tetramethylbiphenyl
a-tetramethylbiphenyl: 2,3,3',4'-tetramethylbiphenyl Structural formulae of the bidentate ligand compounds used in Examples and Comparative Examples are shown blow.

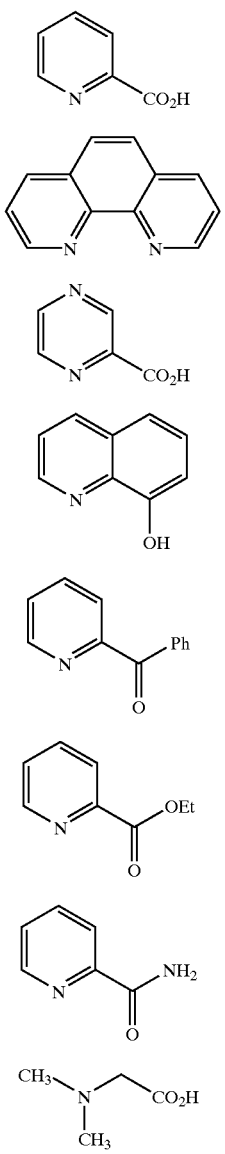

Having the above-described constitution, the present invention brings about the following effects. The present invention provides a novel method for producing biphenyl and its derivatives by oxidative coupling of benzene aromatic compounds. In particular it provides an improved method for selectively producing an asymmetrically substituted biphenyl derivative such as a 2,3,3',4'-biphenyltetracarboxylic acid tetraester by oxidative coupling of a substituted aromatic compound such as a phthalic diester without replenishing with a ligand.

What is claimed is:

1. A method for selectively producing an asymmetrically substituted biphenyl compound comprising oxidatively coupling an aromatic compound represented by formula (1):

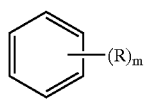

(1)

wherein R represents an alkyl group of 1 to 5 carbon atoms, an alkoxy group of 1 to 5 carbon atoms, an alkoxyl carbonyl group of 1 to 5 carbon atoms, an aryloxy carbonyl group, an alkanoyloxy group of 1 to 5 carbon atoms, an alkanoyloxyalkyl group of 1 to 5 carbon atoms, an alkyl group of 1 to 5 carbon atoms, the hydrogen atom of which is substituted with an acetyl group or a halogen atom, a nitro group, and a halogen atom; and m represents an integer of 1 to 3, in the presence of a palladium salt, a copper salt, and a bidentate ligand compound capable of forming a complex with the palladium salt via the nitrogen atom and the oxygen atom in the molecule thereof in an atmosphere containing molecular oxygen, and wherein the selectivity to the asymmetrically substituted biphenyl compound can be increased 60 to 99%.

2. The method according to claim 1, wherein a phthalic diester is used as the aromatic compound represented by formula (1) to selectively produce a 2,3,3',4'-biphenyltetracarboxylic acid tetraester.

3. The method according to claim 1, wherein the oxidative coupling is carried out at a temperature of 50 to 300° C.

4. A method for selectively producing an asymmetrically substituted biphenyl compound comprising oxidatively coupling an aromatic compound represented by formula (1):

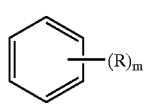

(1)

wherein R represents a an alkyl group of 1 to 5 carbon atoms, an alkoxy group of 1 to 5 carbon atoms, an alkoxyl carbonyl group of 1 to 5 carbon atoms, an aryloxy carbonyl group, an alkanoyloxy group of 1 to 5 carbon atoms, an alkanoyloxyalkyl group of 1 to 5 carbon atoms, an alkyl group of 1 to 5 carbon atoms a hydrogen atom of which is substituted with an acetyl group or a halogen atom, a nitro group, and a halogen atom; and m represents an integer of 0 to 4, in the presence of a palladium salt, a copper salt, and a bidentate ligand compound capable of forming a complex with the palladium salt via the nitrogen atom and the oxygen atom in the molecule thereof in an atmosphere containing molecular oxygen, and wherein the selectivity to the asymmetrically substituted biphenyl compound can be increased 60 to 99%, and wherein the bidentate ligand compound is a nitrogen-containing heterocyclic compound having an oxygen-containing substituent and represented by formula (2):

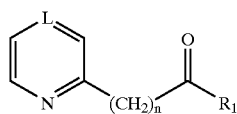

(2)

wherein $R_1$ represents an alkyl group, an aryl group, an alkoxy group, an amino group or a hydroxyl group; L represents CH or N; and n represents an integer of 0 to 3.

5. A method for selectively producing an asymmetrically substituted biphenyl compound comprising oxidatively coupling an aromatic compound represented by formula (1):

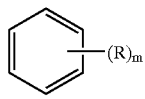

(1)

wherein R represents an alkyl group of 1 to 5 carbon atoms, an alkoxy group of 1 to 5 carbon atoms, an alkoxyl carbonyl group of 1 to 5 carbon atoms, an aryloxy carbonyl group, an alkanoyloxy group of 1 to 5 carbon atoms, an alkanoyloxyalkyl group of 1 to 5 carbon atoms, an alkyl group of 1 to 5 carbon atoms a hydrogen atom of which is substituted with an acetyl group or a halogen atom, a nitro group, and a halogen atom; and m represents an integer of 0 to 4, in the presence of a palladium salt, a copper salt, and, a bidentate ligand compound capable of forming a complex with the palladium salt via the nitrogen atom and the oxygen atom in the molecule thereof in an atmosphere containing molecular oxygen, and wherein the selectivity to the asymmetrically substituted biphenyl compound can be increased 60 to 99%, and wherein the bidentate ligand compound is a nitrogen-containing heterocyclic compound having an oxygen-containing substituent and represented by formula (3):

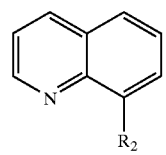

(3)

wherein $R_2$ represents a hydroxyl group or $COR_1$; and $R_1$ represents an alkyl group, an aryl group, an alkoxy group, an amino group or a hydroxyl group.

6. A method for selectively producing an asymmetrically substituted biphenyl compound comprising oxidatively coupling an aromatic compound represented by formula (1):

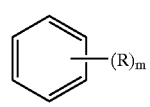

(1)

wherein R represents an alkyl group of 1 to 5 carbon atoms, an alkoxy group of 1 to 5 carbon atoms, an alkoxyl carbonyl group of 1 to 5 carbon atoms, an aryloxy carbonyl group, an alkanoyloxy group of 1 to 5 carbon atoms, an alkanoyloxyalkyl group of 1 to 5 carbon atoms, an alkyl group of 1 to 5 carbon atoms a hydrogen atom of which is substituted with an acetyl group or a halogen atom, a nitro group, and a halogen atom; and m represents an integer of 0 to 4, in the presence of a palladium salt, a copper salt, and a bidentate ligand compound capable of forming a complex with the palladium salt via the nitrogen atom and the oxygen atom in the molecule thereof in an atmosphere containing molecular oxygen, and wherein the selectivity to the asymmetrically substituted biphenyl compound can be increased 60 to 99%, and wherein the bidentate ligand compound is an amino compound represented by formula (4):

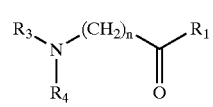

(4)

wherein $R_1$ represents an alkyl group, an aryl group, an alkoxy group, an amino group or a hydroxyl group; $R_3$ and $R_4$ each represent a hydrogen atom, an alkyl group or an aryl group; and n represents an integer of 0 to 3.

* * * * *